United States Patent [19]

Lee et al.

[11] 3,983,037

[45] Sept. 28, 1976

[54] APPARATUS FOR TRANSFER, STORAGE, AND DISTRIBUTION OF LIQUID

[76] Inventors: Jae Yoon Lee; Kuem Ja Lee, both of 1122 Sunny Hill Drive, Columbus, Ohio 43221

[22] Filed: Nov. 5, 1973

[21] Appl. No.: 413,025

[52] U.S. Cl. .................. 210/416 R; 23/258.5 R; 23/259; 128/2 F; 128/233; 128/DIG. 5; 210/DIG. 23
[51] Int. Cl.² .................................................. A61M 1/00
[58] Field of Search ............ 210/94, 416, 444, 440, 210/515, 516, DIG. 23, 455, 446; 233/26; 128/276, 277, 278, 2 F, 216, 231–233, DIG. 5; 23/258.5, 259, 292; 73/425.4 R, 425.6

[56] References Cited
UNITED STATES PATENTS

| | | | |
|---|---|---|---|
| 2,594,621 | 4/1952 | Derrick | 128/278 |
| 3,003,500 | 10/1961 | Barton et al. | 210/94 |
| 3,105,618 | 10/1963 | Whitley | 73/425.6 |
| 3,285,296 | 11/1966 | Ishimaru et al. | 73/425.6 |
| 3,355,098 | 11/1967 | Farr | 233/26 |
| 3,417,750 | 12/1968 | Carson | 128/278 |
| 3,478,889 | 11/1969 | Fessler | 210/361 |
| 3,583,627 | 6/1971 | Wilson | 210/361 |
| 3,698,561 | 10/1972 | Babson | 210/445 |
| 3,706,305 | 12/1972 | Berger et al. | 128/276 |
| 3,706,306 | 12/1972 | Berger et al. | 128/276 |

*Primary Examiner*—Charles N. Hart
*Assistant Examiner*—Robert G. Mukai
*Attorney, Agent, or Firm*—Anthony D. Cennamo

[57] ABSTRACT

This invention is an apparatus for the separation of liquid such as serum or plasma from centrifugated solid particles such as red cells, and for the separation of the liquid into containers for use in an auto-analyzer, and/or storage as well as preservation and distribution of the remainder of the separated liquid samples into other containers.

A single component device is utilized for the separation and distribution of the upper layer of the liquid prepared by centrifugal motion. The apparatus comprises a flexible tubing, a stopper and a capillary tube passing through the system. There is provided the means for the storage of the remainder of liquid, after the adequate amount of samples are obtained and placed in containers for use in an auto-analyzer, and for the easy distribution or transfer of the liquid in the main tube, into other tubes or containers without the need of other apparatus. Several embodiments are illustrated.

1 Claim, 10 Drawing Figures

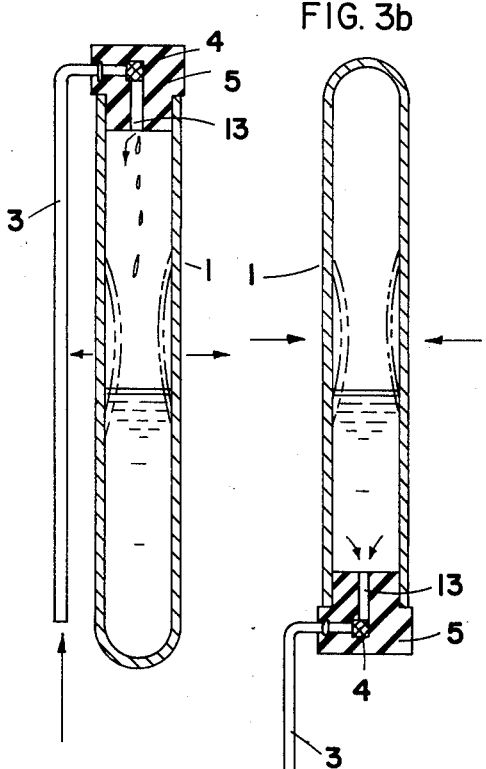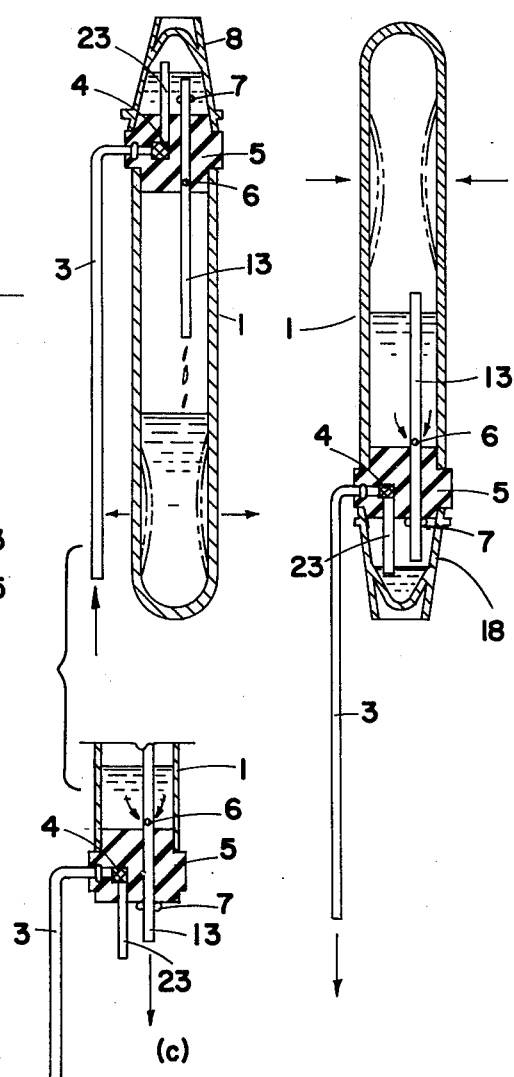

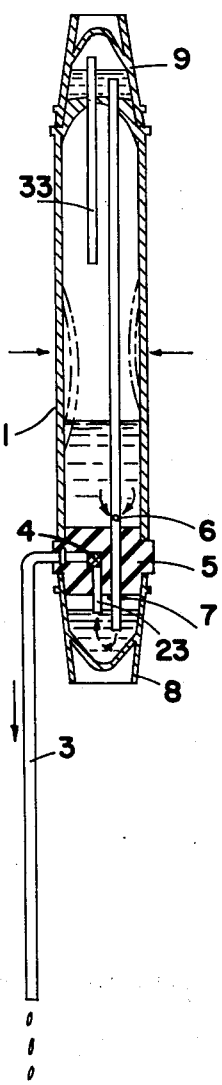

1

APPARATUS FOR TRANSFER, STORAGE, AND DISTRIBUTION OF LIQUID

BACKGROUND

The biochemical tests for the blood and body fluids play an important role in modern medicine. The number of biochemical tests are in both treatment and diagnosis of diseases for the patients requested by doctors are increasing rapidly every year. The increased number of tests are greater than can be handled by the available medical technologists to cause the modern laboratory to resort to automation.

However, the methods and techniques of separation of the serum or plasma from the centrifuged blood has not been improved to meet the need for the speedy automation.

The conventional method for the separation of the serum or plasma into the tube include a glass pipette with a rubber tube at its end. The main disadvantage of the conventional method is the time consuming procedure and the requirement of the three different parts (tube, rubber tube and pipette). These prior art devices cannot get rid of the red cells and fibrin clot which causes problems in automation by clogging the small capillary tubes. The expense of three component materials, the technologist's time spent for the repeated pipetting procedure, and the assembly of parts lend to increase in time and costs. The repeated pipetting between the two tests causes exposure to the medical technologist to the infectious diseases such as hepatitis, etc. Finally, it is necessary with the prior art tubes to cover the serum or plasma tube with a cork, rubber cap, or plastic cap to prevent the evaporation and contamination of the serum or plasma. The cap is also necessary to reduce the exposure of the sample to air which in some instances causes false abnormal values.

New products which become available on the market are not useful by the user mainly due to the lack of speed and convenience of use.

SUMMARY OF INVENTION

A fibrin-free serum separation apparatus which does not require repeated pipetting, nor require any other skill by the medical technologists.

The apparatus is economical in that it does not have unnecessary parts; it prevents medical technologists from exposure to the infectious diseases; and saves medical technologist's time because of the unnecessity of the repeated pipetting and transfer of the serum into the cup or tube. The preferred embodiment basically comprises a flexible tube, a rubber stopper and tubing passing through the stopper. Additionally the preferred embodiment has a filter at the tip of the capillary tube that prevents entering of the fibrin clot into the serum reservoir.

The step of capping the tube in order to prevent the samples from contamination and the evaporation is eliminated with the present invention. The tube itself provides the proper closure of the tube during the entire procedure. With the present invention the sample can be distributed into the several containers to provide specimen for the various tests.

BRIEF EXPLANATION OF THE DRAWINGS

FIGS. 3a and 3b is a side elevation in cross-section of the third embodiment of the invention.

FIGS. 4a and 4b is a side elevation in cross-section of the fourth embodiment of the present invention.

FIGS. 5a and 5b is a side elevation in cross-section of the fifth embodiment of the invention.

DETAILED DESCRIPTION OF DRAWINGS

Figure 1A:
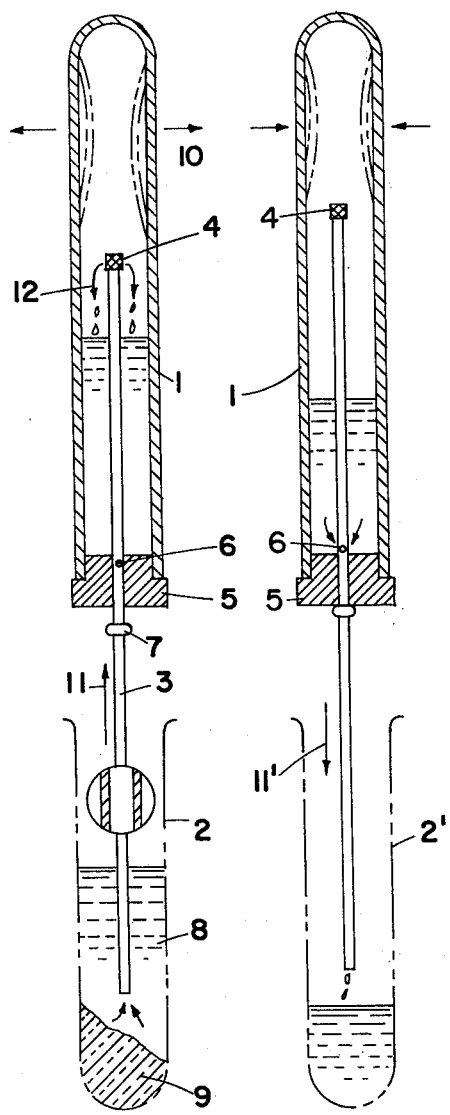
FIGS. 1a and 1b is a side elevation in cross-section of a first embodiment of the present invention.
Figure 1B:
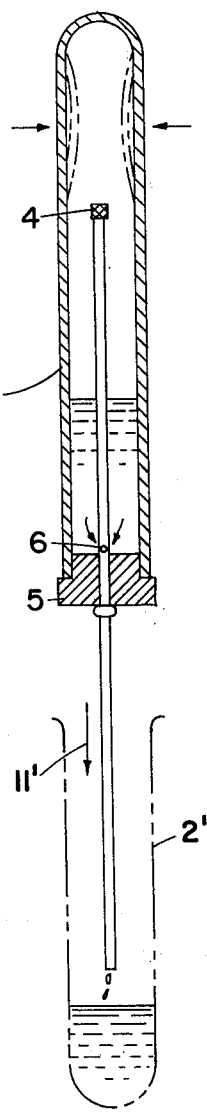

With reference to the illustrations, the detailed description of the invention is as follows:

FIG. 1 shows the apparatus for the transferring of the serum or plasma from the centrifuged blood tube of FIG. 1a and the distribution of the separated serum or plasma into other containers of FIG. 1b. The flexible tube 1 has its mouth closed with the rubber cap 5. Movable capillary tube 3 which penetrates through the middle part of the cap 5 has a filter 4 attached at the tip of the capillary tube extending in the plastic tube. A hole 6 and a projection 7 are made on the middle part of the capillary tube with the distance between the hole 6 and the projection 7 a little longer than the thickness of the cap 5.

In the operation of transferring, for instance the serum or plasma, using the preferred embodiment of FIG. 1a, the capillary tube 3 is inserted into the separated serum or plasma 8 in the blood collecting tube 2 while the hole 6 is entirely closed against the wall of the rubber cap 5. When the flexible plastic tube 1 is released, as the arrow 10 indicates from the pressed state (reverse direction of the arrow) with the fingers, the liquid 8 is transferred through the capillary tube 3, as the arrow 11 indicates, and enters into the tube 1 from the tip of the capillary tube, as the arrow 12 indicates.

The possible fibrin clot in the serum is filtered through the filter 4 attached at the tip of the capillary tube 3. When the desired amount of the serum is transferred and stored in the tube 1, the serum can be distributed into the other container 2'.

Figure 2A:
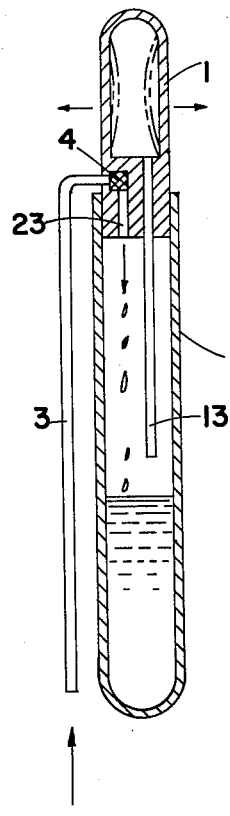
FIGS. 2a and 2b is a side elevation of an embodiment of the present invention.

The apparatus shown in FIG. 2 is slightly different from that of FIG. 1. It consists of three parts, rubber tube or flexible plastic tube 1, glass tube 2 and two capillary tubes 3 and 13 in FIG. 2a. As explained in FIG. 1, the capillary tube 3 is inserted into the centrifuged serum or plasma in the tube. The rubber tube or flexible plastic tube 1 is pressed by fingers and then released, this causes the liquid to be sucked up through the capillary tube 3, then the filter 4, through the capillary tube or plain capillary hole 23, and then, pours into the container or tube 2. The serum or plasma which is separated as explained relative to FIG. 2a, is stored in the container 2 or can be distributed into the other containers.

Figure 2B:
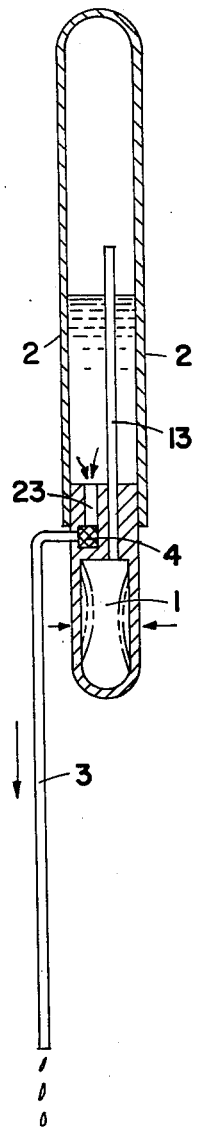

In FIG. 2b, the tube 2 is inverted and the capillary tube 3 is rotated to point the tip downward. While the rubber tube or the flexible plastic tube 1 is repeatedly pressed and released. The liquid is distributed into the other containers through the capillary tubes 23 and 3.

The third embodiment of the invention is illustrated in the FIGS. 3a and 3b.

Similar to that of FIGS. 1 and 2, the capillary tube 3 is put into the serum layer in the tube 1. This is followed by pressure and release of the fingers in order to push the serum or plasma into the tube 1, through the capillary tube 3 and the short capillary tube or plain hole 13 via the filter 4 (shown in FIG. 3a). When the sample in the tube is to be distributed, the tube 1 is turned upside down and the capillary tube 3 is rotated to 180° down, as explained relative to FIG. 2b. The liquid that is the serum layer in the tube 1, is distributed into the other containers via the capillary tube 3, the filter 4, and the capillary tube or plain hole 13, into the other containers by pressing and releasing the flexible tube 1.

In FIG. 4 there is shown another embodiment of the invention. The flexible plastic tube 1 is capped with the rubber, or sealable material 5. The plastic cup 8 covers the rubber cap tightly so as to prevent air leakage. The capillary tubes 3 and 23 and the filter 4 are connected through the cap 5 between the inside of the cup 8 and the outside, and the capillary tube 13 is connected between the inside of the cup 8 and the inside of the tube 1. The length (or height) of the capillary tube 23 from the surface of the cap 8 is slightly longer than that of the capillary tube 13. The hole 6 on the capillary tube 13 is opened when the capillary tube 13 is pushed down until the projection 7 is reached to the top of the cap 5. This distance between the hole 6 and the projection 7 is slightly longer than the thickness of the cap 5. When the tube 1 is released from the pressure exerted by fingers, the liquid is passed through the capillary tube 3, the filter 4, and the capillary tube 23, into the cup 8, covered by the cap 5. Repeated release of the tube 1 from the pressure added by fingers fills the cup 8 with liquid until the surface of the liquid reaches the top of the capillary tube 13. Thereafter, the same amount of liquid sucked up through the capillary tube 3 is passed down into the tube 1 through the capillary tube 13. The entire apparatus is then turned upside down as shown in FIG. 4b. The cup 8 is removed from the cap 5 and used for the auto-analyzer or other intended purpose. When the second cup of sample liquid for distribution is needed, the capillary tube 3 is rotated downwardly and the capillary tube 13 is pushed up until the hole 6 is opened in the tube 1. Then a second cup 18 is placed under the cap 5 as shown in FIG. 4b. Repeated pressure and release of the tube 1 causes the reverse flow of the sample through the hole 6 into the other container after a certain amount of sample liquid is collected in the second cup 18.

These two cups 8 and 18 hold an adequate amount of sample liquid for use in an auto-analyzer. At the same time the manner of the utilization of the apparatus described is very effective in handling the specimen.

The FIG. 4c shows the distribution of the sample into the other container through the capillary tube 3 without the second cup 18. The operation of the capillary tubes 13 and 23 relative to the projection 7 and the hole 6 is the same as that described above.

The FIG. 5 shows still another embodiment of the invention. The principle is the same as in FIG. 4 except that two cups 8 and 9 cover both ends of the tube 1. The liquid is transferred through the capillary tube 3, the filter 4, and the capillary tube 23 into the cup 8. The additional amount of the sample is then passed through the capillary tube 13 into the second cup 9 at the bottom of the tube 1. The extra sample, if it is available is pushed up through the capillary tube 23 and poured off into the tube 1 for the storage or for other distribution. The distribution process is similar to that of FIG. 4a, FIG. 4b, and FIG. 4c.

These embodiments illustrated and described above are very economical, and practical in their usage, and contribute to the health and care for the human life by eliminating the unnecessary complicated steps and unsanitary problems in the separation and distribution of the samples from the centrifuged blood.

Although certain and specific embodiments have been shown and described, it is understood that modifications and departures may be had thereto without departing from the true spirit and scope of the invention.

What is claimed is:

1. Apparatus for medical liquid analysis comprising a flexible liquid tube having an open end, a stopper sealing said open end having an aperture therethrough, a capillary tube passing through said aperture in said stopper and into said flexible tube, a hole in said capillary tube extending in said flexible tube and a projection on said capillary tube on the outside of said stopper, said capillary tube being constructed and arranged to shift between a first position wherein said hole is closed by said stopper and a second position wherein said projection abuts said stopper and said hole is in communication with the interior of said flexible tube, said flexible tube when flexed causes liquid to be sucked up when said capillary tube is in said first position when flexed causes liquid to be expelled when said capillary tube is in said second position; and a filter positioned on said capillary tube extending in said flexible tube.

* * * * *